(12) United States Patent
Kendon

(10) Patent No.: US 7,797,546 B2
(45) Date of Patent: Sep. 14, 2010

(54) PORTABLE STORAGE DEVICE FOR STORING AND ACCESSING PERSONAL DATA

(75) Inventor: Michael Kendon, London (GB)

(73) Assignee: Liberate Software Limited, Whitstable, Kent (GB)

( * ) Notice: Subject to any disclaimer, the term of this patent is extended or adjusted under 35 U.S.C. 154(b) by 1270 days.

(21) Appl. No.: 10/497,014

(22) PCT Filed: Nov. 22, 2002

(86) PCT No.: PCT/GB02/05244

§ 371 (c)(1),
(2), (4) Date: Nov. 9, 2004

(87) PCT Pub. No.: WO03/046827

PCT Pub. Date: Jun. 5, 2003

(65) Prior Publication Data

US 2005/0055560 A1    Mar. 10, 2005

(30) Foreign Application Priority Data

Nov. 22, 2001  (GB) ................................. 0127997.5
Feb. 1, 2002   (GB) ................................. 0202387.7

(51) Int. Cl.
   *G06F 21/00*    (2006.01)
(52) U.S. Cl. .................................................... 713/182
(58) Field of Classification Search ........................ None
   See application file for complete search history.

(56) References Cited

U.S. PATENT DOCUMENTS

| 5,499,293 | A | | 3/1996 | Behram et al. |
| 5,832,488 | A | | 11/1998 | Eberhardt |
| 6,131,090 | A | * | 10/2000 | Basso et al. .................... 706/23 |
| 6,140,936 | A | | 10/2000 | Armstrong |
| 6,862,684 | B1 | * | 3/2005 | DiGiorgio .................... 713/163 |
| 2002/0046061 | A1 | | 4/2002 | Wright et al. |
| 2002/0120470 | A1 | | 8/2002 | Trice |
| 2002/0123909 | A1 | * | 9/2002 | Salisbury ........................ 705/3 |

FOREIGN PATENT DOCUMENTS

| EP | 0 869 460 A2 | 10/1998 |
| FR | 2 809 211 | 11/2001 |
| WO | WO 99/22340 | 5/1999 |

OTHER PUBLICATIONS

PCT Search Report for PCT/GB02/05244, mailed Mar. 18, 2003, 3 pages.

* cited by examiner

*Primary Examiner*—Brandon S Hoffman
(74) *Attorney, Agent, or Firm*—Blakely, Sokoloff, Taylor & Zafman LLP

(57) ABSTRACT

A method of securely storing and accessing personal data (26) relating to an individual (28), said personal data constituting a personal data record, is described. The method comprises: coupling a portable data storage device (42) to a computing device (12) for data transfer between them, the storage device carrying an encrypted personal data record (38) and a decryption means (40) for decrypting the personal data record upon provision of a key (36) not stored on the storage device (42); accessing the personal data record on the storage device (42) and running the decryption means (40) on the computing device (12) to decrypt the personal data record upon input of the key (36) to the computing device; and displaying the decrypted personal data (26) by means of the computing device.

43 Claims, 13 Drawing Sheets

```
var strCrypt="FF...FF"        /* variable containing the encrypted html page
var strPassword = "xxxxxx..."  /* variable containing the password function decrypt(strPassword)  /* function as part of the encryption/decryption
                               /* code. Password passed as a parameter. The
                               /* string to be decrypted is referenced directly.

{
        var strOutBuf          /* variable to contain the decrypted html

/* execute decryption logic
        /* in this case "Blowfish"
        /* decrypts into a buffer strOutBuf document.clear();
        document.write(strOutBuf);  /* creates a new html page on the fly in
                                    /* temporary storage.
}
```

FIG. 4a    40

```
1   <html>                                              60
2   <head>
3   <script language = "javascript" src = "bfish.js">
4   </script>
5   <script language = "javascript">
6   var strCrypt =
7   "EB83C343437E558DFFAEAD5E512AD0F67CD114F
8   04EBA55CA6B07A31B21.....";
9   </script>
10  </head>
11  <body>
12  <script language = "javascript">
13  decrypt (parent.get_V01());
14  </script>
15  </body>
16  </html>
```

FIG. 4b

Medical Record Print For
Mary Brown

Cardholder Details.....

| | |
|---:|:---|
| SURNAME | Brown |
| FORENAME | Mary |
| MIDDLE NAMES | Elizabeth |
| TITLE | Ms |
| GENDER | Female |
| DATE OF BIRTH | 21st May 1958 |
| | |
| OCCUPATION | Stenographer |
| MEDICAL INSURER | TrustMedics |
| MEMBERSHIP NO. | TM65/667/G/888 |
| N.I. NUMBER | YY 02 56 95 B |
| RELIGION | Anglican |
| | |
| CARD HOLDER ADDRESS | 12, Umber Drive |
| | Little Ochre |
| | Middleton |
| | Midshire |
| POST CODE MD4 6XX | MD4 6XX |
| COUNTRY | UNITED KINGDOM |
| DAYTIME TELEPHONE | 0123456789 |
| EVENING TELEPHONE | 0123987654 |
| MOBILE TELEPHONE | 07778654321 |
| FAX NUMBER | 0123456789 |
| E-MAIL ADDRESS | mbrown@rustmail.co.uk |
| | |
| PASSPORT NUMBER | 043591248 |
| PASSPORT ISSUE DATE | 5th July 1996 |
| PASSPORT EXPIRY DATE | 5th July 2006 |
| COUNTRY OF BIRTH | England |
| NATIONALITY | British |
| | |
| HEIGHT | 1.625 metres |
| WEIGHT | 87 kg |
| HAIR COLOUR | Brown |
| EYE COLOUR | Brown |
| DISTINGUISHING FEATURES | Birthmark on left shoulder |

FIG. 8a

Next Of Kin Details...

| | |
|---|---|
| SURNAME | Brown |
| FORENAME | Henry |
| TITLE | Mr |
| RELATIONSHIP TO CARDHOLDER | Father |
| ADDRESS | 77, Rustic Avenue |
| | Lisswold |
| | Winchester |
| | Hampshire |
| POSTCODE | WS5 6ZZ |
| COUNTRY | United Kingdom |
| DAYTIME TELEPHONE | 01265 817324 |
| EVENING TELEPHONE | 01265 817324 |
| MOBILE TELEPHONE | 0779 6665 4443 |
| FAX NUMBER | 01265 817324 |
| E-MAIL ADDRESS | |

General Practitioner's Details...

| | |
|---|---|
| SURNAME | Davies |
| FORENAME | James |
| TITLE | Dr |
| ADDRESS | The Grange Surgery |
| | Middleton |
| | Midshire |
| POSTCODE | MD2 8XX |
| COUNTRY | United Kingdom |
| DAYTIME TELEPHONE | 01233 654734 |
| EVENING TELEPHONE | |
| MOBILE TELEPHONE | 07771 804321 |
| FAX NUMBER | |
| E-MAIL ADDRESS | grange.surgery@docnet.co.uk |

Alerts...
Severe reaction to nuts - Epipen carried
Diabetic

Allergies...
Nut allergy
Lactose intolerant

Current Medication...
4th August 2002 Losec 10 mg 1 times daily
16th May 1993 Metaformin 500 mg 3 times daily

Previous Medication...
4th September 1997 to 8th September 1997 Otrivine nasal spray As required Stopped due to nose bleeds
July 1996 to August 1996 Distalgesic 1 tablet 3 times daily

FIG. 8b

Medical Event Summary...
DATE  MEDICAL EVENT
4th August 2002  Gastritis
4th June 1996  Fractured Left femur
8th May 1993  Diabetes

Medical Event Summary...
EVENT DATE  4th August 2002
EVENT DESCRIPTION  Gastritis
TREATMENT  Medication
MEDICATION PRESCRIBED  Losec 10 mg 1 times daily
PRESCRIPTION START DATE  4th August 2002
INVESTIGATIONS  None Recorded.
SPECIALISTS  None Recorded EVENT DATE  4th June 1996
EVENT DESCRIPTION  FracturedLeft femur
TREATMENT  Set In plaster
MEDICATION PRESCRIBED  Distalgesic 1 tablet 3 times daily
PRESCRIPTION DATES  July 1996 to August 1996
INVESTIGATION DATE  4th June 1996
INVESTIGATION DETAILS  Fractured Left femur
SPECIALIST / DOCTOR  Mr Gregory Maidenn
SPECIALITY  Orthopaedic surgeon
SEEN ON  4th June 1996

EVENT DATE  8th May 1993
EVENT DESCRIPTION  Diabetes
TREATMENT  Confirmation of Condition
MEDICATION PRESCRIBED  Metaformin 500 mg 3 times daily
PRESCRIPTION START DATE  16th May 1993
INVESTIGATION DATE  8th May 1993
INVESTIGATION DETAILS  Suspected diabetes
SPECIALIST / DOCTOR  Doctor Andrew Lane
SPECIALITY  Diabetes Consultant
SEEN ON  8th May 1993
REASON  Suspected diabetes

Investigations...
DATE  4th June 1996
INVESTIGATION  Fractured Left Femur
TEST(S)
DATE                TYPE OF TEST       TEST OF RESULT
4th June 1996   X ray  Left leg        Abnormal Result: Fracture Shaft of Femur DATE  8th May 1993
INVESTIGATION  Suspected diabetes
DATE  8th May 1993
INVESTIGATION  Suspected diabetes
TEST(S)
DATE                TYPE OF TEST       TEST OF RESULT
15th May 1993   Kidney Tests           Urea: 7
                                       Potassium: 48
                                       Sodium: 145
                                       Creatinine:
14th May 1993   Diabetes               HbA1: 7%
                                       Blood Glucose: 10mm

FIG. 8c

SURNAME Lane
FORENAME Andrew
TITLE Doctor
SPECIALITY Diabetes Consultant
ADDRESS 599 Harley Street
London
POSTCODE
COUNTRY W1
DAYTIME TELEPHONE
EVENING TELEPHONE 020 7936 0000
MOBILE TELEPHONE
FAX NUMBER
E-MAIL ADDRESS

REFERRALS / VISITS    VISIT DATE    MEDICAL EVENT

SURNAME Maidenn
FORENAME Gregory
TITLE Mr
SPECIALITY Orthopaedic surgeon
ADDRESS Middleton General Hospital
Giles Lane
Middleton
Midshire
POSTCODE MD6 9XX
COUNTRY United Kingdom
DAYTIME TELEPHONE 01334 782913
EVENING TELEPHONE
MOBILE TELEPHONE 07899 211312
FAX NUMBER
E-MAIL ADDRESS maidenn@internet.com REFERRALS / VISITS    VISIT DATE      MEDICAL EVENT
                      4th June 1996   Fractured Left Femur

FIG. 8d

Immunisations...
4th March 1998 Tetanus
1962 Polio
1955 Diphtheria

Eye Test Details...
DATE 4th October 2001
OPTOMETRIST
WHERE TESTED SupaSpecs
ADDRESS 51 The High Street
Middleton
Midshire
POSTCODE MD7 4LX
COUNTRY United Kingdom
DAYTIME TELEPHONE 01487 845734
EVENING TELEPHONE
MOBILE TELEPHONE
FAX NUMBER
E-MAIL ADDRESS

Right eye

|       | Sphere | Cyl. | Axis | Prism | Base |
|-------|--------|------|------|-------|------|
| Dist. | 2.00   | 0.25 | 60   |       |      |
| Near  |        |      |      |       |      |

Letf eye

|       | Sphere | Cyl. | Axis | Prism | Base |
|-------|--------|------|------|-------|------|
| Dist. | 2.00   |      |      |       |      |
| Near  |        |      |      |       |      |

SUPPLEMENTARY DETAILS

Right eye

|       | Sphere | Cyl. | Axis | Prism | Base |
|-------|--------|------|------|-------|------|
| Dist. |        |      |      |       |      |
| Near  |        |      |      |       |      |

Letf eye

|       | Sphere | Cyl. | Axis | Prism | Base |
|-------|--------|------|------|-------|------|
| Dist. |        |      |      |       |      |
| Near  |        |      |      |       |      |

COMMENTS  Bifocal Single Vision

Lifestyle Details...
Smokes 20 Cigarettes per day.
Drinks 6 units of alcohol per week.
Jogs 3 miles per day
Scuba diving

All Details Recorded Up To 29th August 2002

FIG. 8e

PORTABLE STORAGE DEVICE FOR STORING AND ACCESSING PERSONAL DATA

Cross-Reference to Other Applications

This Application is a National Phase of International Application No. PCT/GB02/05244, filed on Nov. 22, 2002, which claims priority from Great Britain Patent Application No. 0127997.5, filed on Nov. 22, 2001, and Great Britain Patent Application No. 0202387.7, filed on Feb. 1, 2002.

TECHNICAL FIELD

The present invention concerns improvements relating to securely storing and accessing personal data It relates particularly, although not exclusively, to the secure storage of personal data (such as medical information) on a credit-card sized CD-ROM, and the secure access to this information using a key that is not stored on the CD-ROM.

BACKGROUND ART

In the current information age, an ever increasing amount of information relating to individual citizens is being collected, stored and analysed. For example, the use of credit, debit and loyalty cards enables banks and other organisations to analyse an individual's spending habits and target them with unsolicited offers of loans etc. However unwelcome these offers are to an individual, it is rarely considered that information collected about that individual could be used for unlawful purposes or against the interests of the individual. Fortunately, there are data protection laws in most countries that give individuals certain rights in the data that is collected about them.

In the United Kingdom, anyone processing (including obtaining, holding, and disclosing) personal data must comply with the eight enforceable principles of good practice. According to these principles data must be: fairly and lawfully processed; processed for limited purposes; adequate, relevant and not excessive; accurate; not kept longer than necessary; processed in accordance with the data subject's rights; secure; and not transferred to countries without adequate protection.

Despite the drawbacks of collating information mentioned above, the recordal of data relating to an individual can be empowering to that individual. One area in which this is particularly true is in the field of medicine. The use of computers in medicine has facilitated the processing and storage of electronic medical records in order to better serve the interests of the individual and of the community. Computers contribute towards better medical care by automating techniques, reducing the burden on the doctor's memory and assisted in the compilation of medical records. Medical computer systems meet the new demands of specialisation and teamwork by providing quick and selective access to information on the patient and their treatment thereby ensuring continuity in medical care. Medical data processing also brings a major improvement to hospital management and in this way it can help to reduce the cost of health care. Computers have many uses in recording the admission, transfer and release of patients, keeping track of diagnostic and therapeutic activities, medication, laboratory analysis, accounting, invoicing etc. Lastly, medical data processing represents an indispensable instrument for medical research and for a policy of early and systematic diagnosis and prevention of certain diseases.

Accordingly, personal health data appear in many files which can be stored on, and accessed by, a computer. The holders of these files vary: the general medical practitioner, the hospital doctor, the school doctor, the occupational health worker, the hospital administrator, social security offices, and so on. Usually, the recording of medical data occurs in the context of the doctor-patient relationship. It takes the form of a medical record to be used in making the diagnosis and in supervising and treating the patient. In the context of this confidential relationship freely chosen by the patient, the information is obtained with the patient's consent by the doctor or a member of the medical team who is required to observe confidentiality under the rules of professional ethics. Health records may also be established outside the context of the doctor-patient relationship and may include data concerning perfectly healthy persons. The recording of information is sometimes imposed by a third party, perhaps even without the explicit consent of the data subject.

The quality and integrity of information is extremely important in matters of health. At a time of increasing personal mobility, the exchange of accurate and relevant medical information is necessary for the individual's safety. Furthermore, the development of medical science depends on a transborder flow of medical data and the setting up of specialised information systems over considerable geographical distances (such as the Eurotransplant organisation for the transplantation of human organs).

The needs which medical data processing systems have to satisfy are often contradictory. Information must be readily available to duly authorised users whilst remaining inaccessible to others. The obligation to respect the patient's privacy places certain restrictions on the recording and dissemination of medical data, whereas the right of each individual to health implies that everyone should benefit from the progress made by medical science thanks to intensive use of medical data.

Due to the sensitive nature of medical data, certain of the contents of medical files may harm the patient if used outside the doctor-patient relationship. Unauthorised disclosure of personal medical data may therefore lead to various forms of discrimination and even to the violation of fundamental rights. In view of these problems, it has become highly desirable that the operation of every automated medical file should be subject to a specific set of regulations. The general purpose of these regulations should be to guarantee that medical data are used not only so as to ensure optimum medical care and services, but also in such a way that the data subject's privacy and dignity are fully respected.

Some individuals are not content with knowing that their medical data is being handled according to the principles of data protection, but demand to be in control of their own data. This is likely to be of growing significance as new and experimental medical techniques become more widespread. Even today, the results of genetic testing can blight an individual's life if the results indicate that the individual is predisposed towards a particular disease or condition. It is therefore of the utmost importance that access to this information can be controlled by the patient in a secure manner.

There are numerous ways in which an individual may collect and securely store information about themselves, but few which are secure and offer true portability. Whilst pocket computers and hand-held devices offer secure storage, they are bulky, expensive and have only a limited capacity to share information with others. They also require sophisticated procedures to minimise problems if they are lost. In recent years the techniques and facilities adopted for the secure storage and access of data have become more sophisticated, involving chip-carrying smart cards, for instance, and complex systems utilising multiple passwords, biometric keys, and expensive encryption algorithms. While such developments in technology are to be commended, they are unlikely to be used by health authorities and other organisations which have limited funds and are therefore unlikely to be willing to install expensive dedicated smart card readers or biometric input data devices.

It is therefore desired to provide a method and system of securely storing and accessing data which overcomes or substantially reduces the above mentioned problems.

DISCLOSURE OF INVENTION

According to a first aspect of the invention there is provided a method of securely storing and accessing personal data relating to an individual, said personal data constituting a personal data record, the method comprising coupling a portable data storage device to a computing device for data transfer between them, the storage device carrying an encrypted personal data record and a decryption means for decrypting the personal data record upon provision of a key not stored on the storage device; accessing the personal data record on the storage device and running the decryption means on the computing device to decrypt the personal data record upon input of the key to the computing device; and displaying the decrypted personal data by means of the computing device.

An advantage of the invention is that it provides a simple, fast and secure way of storing and accessing personal data. It also gives an individual control of their own data. Another advantage of the invention is that the key required to decrypt the data stored on the portable storage device is not stored on the device itself. This means that the encrypted data stored on the device will not be readable should the device fall into the hands of an unauthorised third party who is not in possession of the key. The features of portability and security of the portable storage device also enable an individual to take control of their own data, so that they may provide their data to whomever they choose in a manner in which the data recipient will have confidence in its authenticity.

Storing the decryption means such as an encryption or decryption engine on the device itself, but running the encryption engine on the computing device, is another key feature of the invention. The result of this feature is that the portable storage device may comprise a dumb device (such as a read-only CD, or a USB memory stick) that does not require a chip or other means for carrying out processing on the device itself. Fairly complex and computationally intensive decryption algorithms can therefore be utilised with the method of the invention without unduly restricting the amount of personal data which can be stored on the device.

By personal data record, it is generally meant any collection or record of personal data which relates to an individual that the individual wishes to keep secure and out of the hands of any unauthorised third parties. Such data may, for example, be medical data (including details about an individual's behaviour and lifestyle), financial data (such as details of the individual's share portfolio, pension contribution history etc), or even educational data (e.g., grades achieved in examinations and attendance records).

There is preferably associated with the personal data an indication of the level of security to be attributed to the data. The security level indictor determines the particular key which is to be used for encrypting (and therefore decrypting) personal data thereby controlling to whom access to the data should be granted or denied. Thus data with a high level of security may only be accessed by the owner of the data, and data with a lower level of security may be accessed by the owner of the data and an authorised third party. It is envisaged that a number of different security levels could be provided to control data access to different groups of authorised third parties. Other types of data may be subject to no security controls at all. In this way, it is possible for an individual to choose to make critical or very important personal data available in situations where the data owner is unable to provide a key to decrypt the data stored on the device.

Most preferably the personal data is displayable in read-only form. This advantageous feature provides an additional level of security by virtue of the fact that no additional or changed personal data can be saved on the computing device, and personal data on the device itself cannot be amended or deleted.

The personal data is advantageously embedded in a page viewable, when unencrypted or decrypted, by an Internet browser running on the computing device.

In a preferred embodiment, the encrypted personal data includes at least one address of a remote data storage facility which is accessible via the computing device. When the personal data is decrypted by the decryption means, the computing device is thus able to address encrypted additional personal data held at the addressed remote data storage facility. The encrypted personal data can also include at least one access code which, when decrypted by the decryption means, enables access to the encrypted additional personal data held by the addressed remote data storage facility. The advantage of this feature of the invention is that data which may be too large to be stored on the portable storage device itself can be displayed by effectively using the device to unlock or enable access to the additional data. Another benefit of this feature is that access to the additional data will only be provided to a user who is in possession of both the portable storage device and the key. A user in possession of only one of these will therefore not be able to gain access to the additional data on the remote storage facility. The access codes may be provided in a page on the device separate from personal data, or they may be included in a page which contains personal data.

The key which is input to the computing device for decrypting the personal data is preferably also used to decrypt the encrypted additional personal data, and thus this additional personal data can also be displayed by the computing device. An advantage of using the same key for providing access to the additional data stored at the data storage facility and for displaying the data stored on the portable storage device is that only one password needs to be remembered, if a password is to serve as the key.

The method may further comprise writing encrypted additional personal data from the remote data storage facility to the portable data storage device via the computing device. This enables the personal data held on the portable data storage device to be updated quickly and easily. This step may be preceded by uploading personal data to the remote data storage facility and encrypting that data. This step can be carried out by the owner of the data, or by an authorised third party. If the data owner does not have the facilities to write encrypted additional personal data from the remote data storage facility to the portable data storage device, then a replacement portable storage device bearing the encrypted additional personal data may be issued to him. This may be carried out automatically every time additional data is uploaded to the remote data storage facility, on request, or at regular time intervals.

The method may also comprise the step of checking a date or identity code held by a portable data storage device and preventing access to the personal data stored on the portable data storage device if the date or identity code indicates that access should no longer be allowed because that portable data storage device is out of date or has been superseded. This additional security facility meets the data protection recommendation of not keeping the data longer than necessary.

Yet another security feature is provided by recording and auditing access to the remote data storage facility. If an unauthorised third party is attempting to access data which he does not have permission to access, the data owner may thus be informed and take any action he or she deems appropriate.

According to a second aspect of the invention there is provided a system for securely storing and accessing personal data relating to an individual, said personal data constituting a personal data record, the system comprising: a portable data storage device carrying an encrypted personal data record and a decryption means for decrypting the personal data upon provision of a key not stored on the storage device; a computing device to which the portable data storage device can be coupled for data transfer between them, the computing device including means for accessing the personal data record on the storage device, and means for running the decryption means to decrypt the personal data record upon input of the key to the computing device; and a display associated with the computing device for displaying the decrypted personal data.

Preferably the computing device is a personal computer, a personal digital assistant, or any other suitable computing device which has a portable storage device reader.

Preferably the encrypted data is in the form of encrypted Web pages, and the display means is a Web or Internet browser. The Web pages are preferably written in hypertext markup language (HTML). They may, however, be written in extensible markup language (XML) or any other suitable markup language. The advantage of these features is that dedicated software to read personal data from the device is not necessary. This reduces the costs associated with implementing the system: Web browsers are available as freeware, and special training to use the system is not required. Most preferably an encrypted Web page is embedded in a container file which includes code to access the decryption means. The container file is preferably written in HTML.

The Web pages may be created using a text editor or, alternatively, they may be created using software packages such as DreamWeaver™ or FrontPage™. Most preferably a scripting environment such as Microsoft Active Server Pages (ASP) is used to generate the Web pages automatically. ASP's are text files that contain not only text and HTML tags (as in standard Web pages), but also commands written in a scripting language (i.e. a simple programming language designed to perform special or limited tasks) such as Javascript.

The system preferably also includes a remote data storage facility. Connection between the computing device and the remote storage facility may be made via the Internet using the hypertext transfer protocol (HTTP). However, personal data could be sent between the two devices via file transfer protocol (FTP), or by using other suitable protocols.

Further preferred features of the system are set out in appended claims.

A portable data storage device for use in the method and/or system described above is also provided, the device carrying encrypted personal data and a decryption means for decrypting the personal data upon provision of a key not stored on the device itself, and being co-operable with a computing device to which the portable data storage device can be coupled for data transfer between them, whereby the computing device can access the personal data on the storage device, run the decryption means to decrypt the personal data upon input of the key, and drive an associated display to display the decrypted personal data.

Preferably the portable storage device comprises an optical disk such as a compact disk (CD). Most preferably the CD is read-only (otherwise known as a CD-ROM), although a rewritable CD may be used. The CD (whether read-only or writable) is preferably the size and shape of a conventional credit card so that it may be easily carried about an individual's person.

The decryption means preferably includes scripting language (e.g. Javascript) code for decrypting the encrypted pages.

Each Web page preferably includes means for addressing and accessing a remote storage facility via the computing device to enable the computing device to address encrypted additional personal data held at the remote data storage facility. This means may be provided in the form of a hyperlink.

Most preferably the device carries means for launching a program, such as a Web or Internet browser, on the computing device to display unencrypted or decrypted personal data when the device has been coupled to the computing device.

BRIEF DESCRIPTION OF DRAWINGS

Preferred embodiments of the invention will now be described, by way of example only, with reference to the accompanying Figures, in which:

FIG. 4a shows a pseudo-code fragment for implementing a decryption algorithm for decrypting encrypted personal data;

FIG. 4b is an HTML document containing an encrypted Web page;

FIGS. 8a to 8e show a personal data record containing personal medical data relating to a patient;

DETAILED DESCRIPTION OF THE PREFERRED EMBODIMENTS

Figure 1:
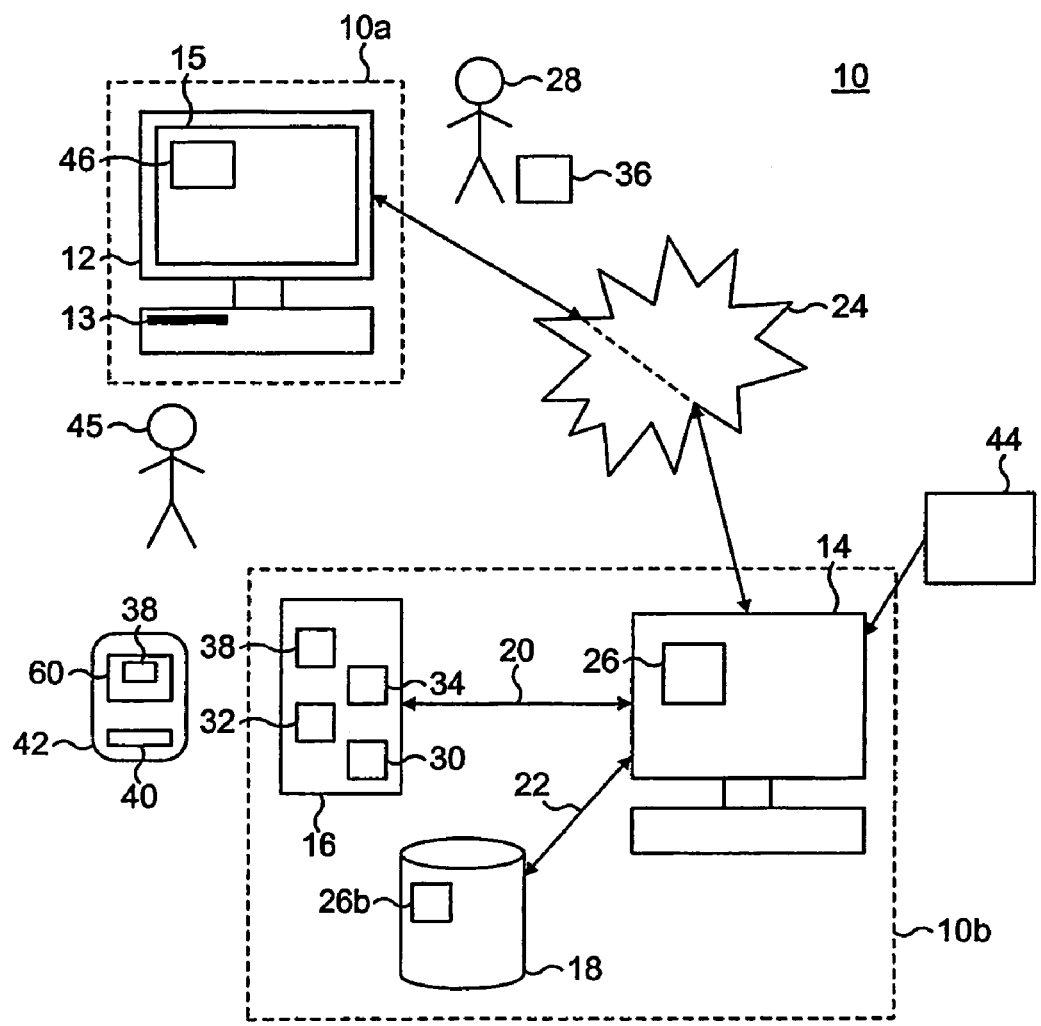
FIG. 1 is a diagram of a client-server system suitable for implementing preferred embodiments of the invention.

Referring firstly to FIG. 1 of the drawings, there is shown a system 10 which is suitable for implementing preferred embodiments of the present invention, the system 10 comprising a client-side 10a and a server-side 10b. The client-side 10a of the system 10 comprises a client computer 12 which includes a portable storage device reader 13. The client computer 12 also has an Internet or Web browser 15 provided for displaying Web pages 46.

The server-side 10b of the system 10 includes a server computer 14 connected to a portable storage device production facility 16 and an optional secure database 18 via respective connections 20 and 22. The client computer 12 may be connected to the server computer 14 via the Internet 24. The double-headed arrows on the connections shown in FIG. 1 indicate that data can be exchanged in both directions between the client computer 12 and the server computer 14, and between the server computer 12 and the optional database 18 and the portable storage device production facility 16.

The server computer 14 is arranged to host a data storage facility which provides a central resource for storing personal data 26 relating to an individual 28. The data storage facility includes a database management system (not shown) for managing incoming data 26, and for logging, filing and retrieving data 26. The portable storage device production facility 16 includes an encryption engine 30 for encrypting data 26, a Web page production facility 32 for producing Web pages 46, and a portable storage device writing facility 34 for writing data to portable storage devices 42. A call centre 44 in communication with the server 14 is also provided, the function of which will be explained later.

When an individual 28 (who will typically be the owner of the data) wishes to securely store his personal data 26 at the data storage facility, he generates an encryption password 36 which is sent to the data storage facility together with his personal data 26. His personal data 26 and his encryption password 36 are then transmitted to the portable storage device production facility 16 via connection 20, and the data 26 is then encrypted by the encryption engine 30 using the encryption password 36. The encrypted Web page data 38 is then passed to the portable storage device writing facility 34. Next, the encrypted data and a decryption engine 40 for decrypting this encrypted data are written to a portable storage device 42. The portable storage device 42 is then issued to the individual 28.

When the data owner 28 (or a third party 45) wishes to access the personal data 26 stored on the portable storage device 42, the device 42 is inserted into a portable storage device reader 13, and the encrypted data stored thereon is decrypted by means of the decryption engine 40 and the data owner's encryption password 36. Additional personal information 26b relating to the individual 28 that is stored (optionally in the database 18) at the data storage facility (but not on the portable storage device 42 itself) may also be accessed using the portable storage device 42 as an access means.

The methods by which personal data 26 is sent to, and stored at, the data storage facility, and by which the portable storage device 42 is produced and used to securely access personal data will now be described in more detail with reference to FIGS. 2 to 6.

Figure 2:
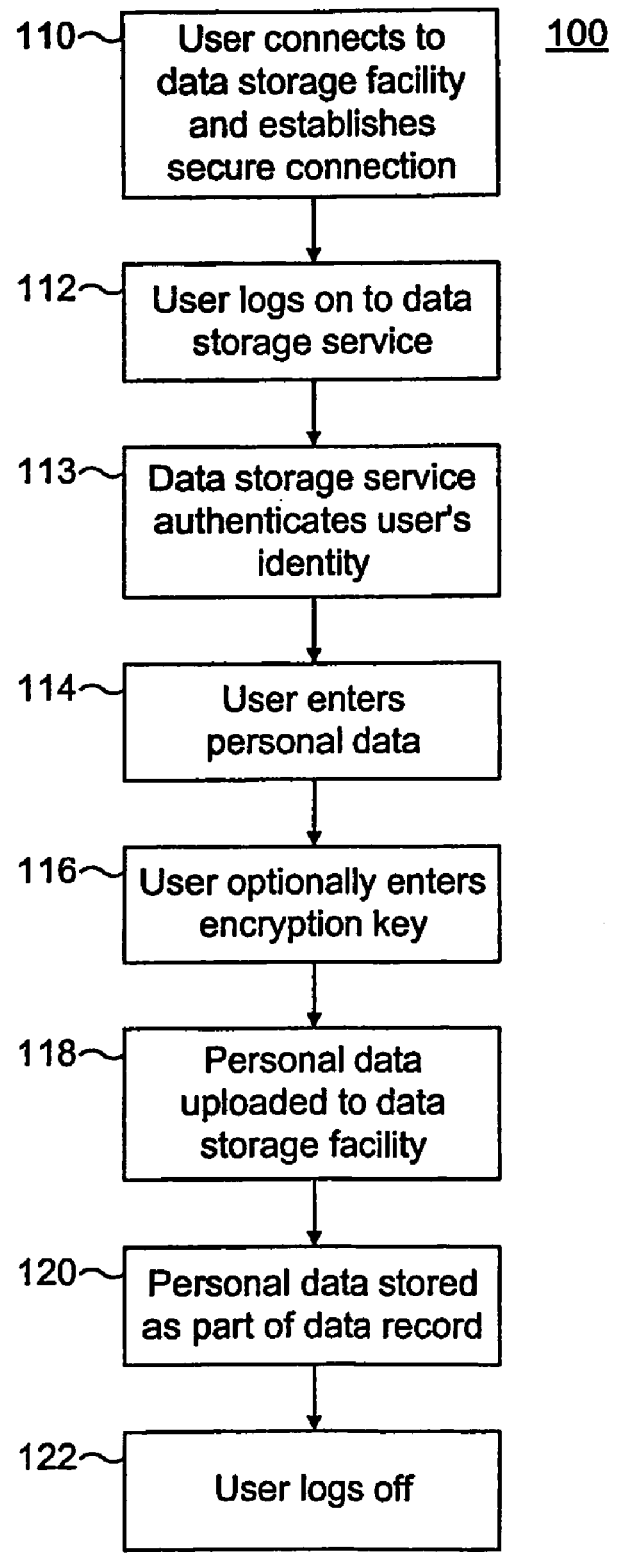
FIG. 2 is a flow diagram showing the steps involved in uploading personal data to a data storage facility.

Firstly, the steps of the method 100 by which personal data 26 relating to an individual 28 is sent to, and stored at, the data storage facility are discussed with reference to the flow diagram of FIG. 2. The method 100 commences with the owner of the data 28 (or an authorised third party 45) connecting at Step 110 to the data storage facility by way of a secure Internet connection between the client computer 12 and the server computer 14 which hosts the facility. A secure connection may be established using standard Internet public encryption techniques, making the communication of data between the client 12 and the server 14 extremely secure.

Upon receiving a request for access to the data storage facility, the server computer 14 sends a "start-up" Web page 46 to the client computer 12 for display in the Web browser 15. The start-up Web page 46 displays a request for the data owner 28 to confirm his identity. The data owner 28 then logs onto the data storage facility at Step 112 by providing a user ID to confirm his identity. If the data owner 28 is using the data storage facility for the first time, then Step 112 must be preceded by the data owner registering with the service in order to receive a user ID to access the service. This type of registration process will be well-known to one skilled in the art, and will therefore not be discussed in any further detail.

The data storage facility then authenticates at Step 113 the data owner's identity. If the data owner 28 is authorised to access the data storage facility, a Web page suitable for entering data is sent to the data owner's Web browser 15. Next, the data owner 28 enters at Step 114 the personal data 26 that he wishes to store at the data storage facility, and indicates the level of access to be granted to the personal data 26. This may be done by the data owner 28 simply filling out the relevant parts of a displayed Web form, or by clicking on check boxes and/or radio buttons. The data owner 28 then enters at Step 116 an encryption password 36 that will be used as a key to encrypt his personal data 26. This latter step is generally only carried out when the data owner 28 is using the data storage facility for the first time, or he has lost his personal storage device 42 and/or wishes to change his encryption password 36.

When the data owner 28 has entered all of the personal data 26 that he would like to store at the present time, he clicks on (for example) a "submit" button displayed on the Web page, and his personal data is uploaded at Step 118 to the server computer 14 from the client computer 12 via a secure Internet connection. The individual's personal data 26 is subsequently stored at Step 120 as part of his personal data record 48 at the data storage facility. If the server computer 14 has the facilities for storing data, then the personal data 26 may be stored on the server computer. Alternatively, if the data storage facility is provided by one or more databases 18, the method 100 may include the further step of transmitting personal data 26 from the server computer 14 to a database 18 (via a secure connection, if necessary). The data owner 28 then logs off or disconnects at Step 122 from the data storage facility.

The above described Steps 110 to 118 may also be carried out where the individual wants to amend his personal data 26 which is stored at the data storage facility. However, if amendments are being made to the data, details (such as the time, date, identity of the user accessing the data, and the type of access e.g. read, write, update) of those amendments are logged at the data storage facility to provide a history of who has done what to the personal data 26, and when.

In one embodiment of the invention, instead of (or in addition to) the data owner 28 submitting personal data 26 to the data storage facility via the Internet 24, this data may be sent to the storage facility via a call centre 44. The call centre 44 would be accessible by post for submitting data on physical media (such as paper or X-ray film), or even by telephone and email. The data owner 28 would need to submit his user ID to the call centre 44 in order to be granted permission to access the data storage facility. This ensures that only an authorised person can access and amend data stored at the facility.

If an individual 28 attempts to log on to the data storage facility a predetermined number of times with an incorrect user ID, he could be barred from accessing the storage facility. In a manner akin to that used in telephone banking, the individual 28 might have to contact the call centre 44 to reaffirm his identity. This embodiment of the invention not only provides an additional level of security for individuals 28 using the data storage facility, but individuals are not restricted to using the Internet for amended or adding data 26 to their personal data record 48.

Figure 3:
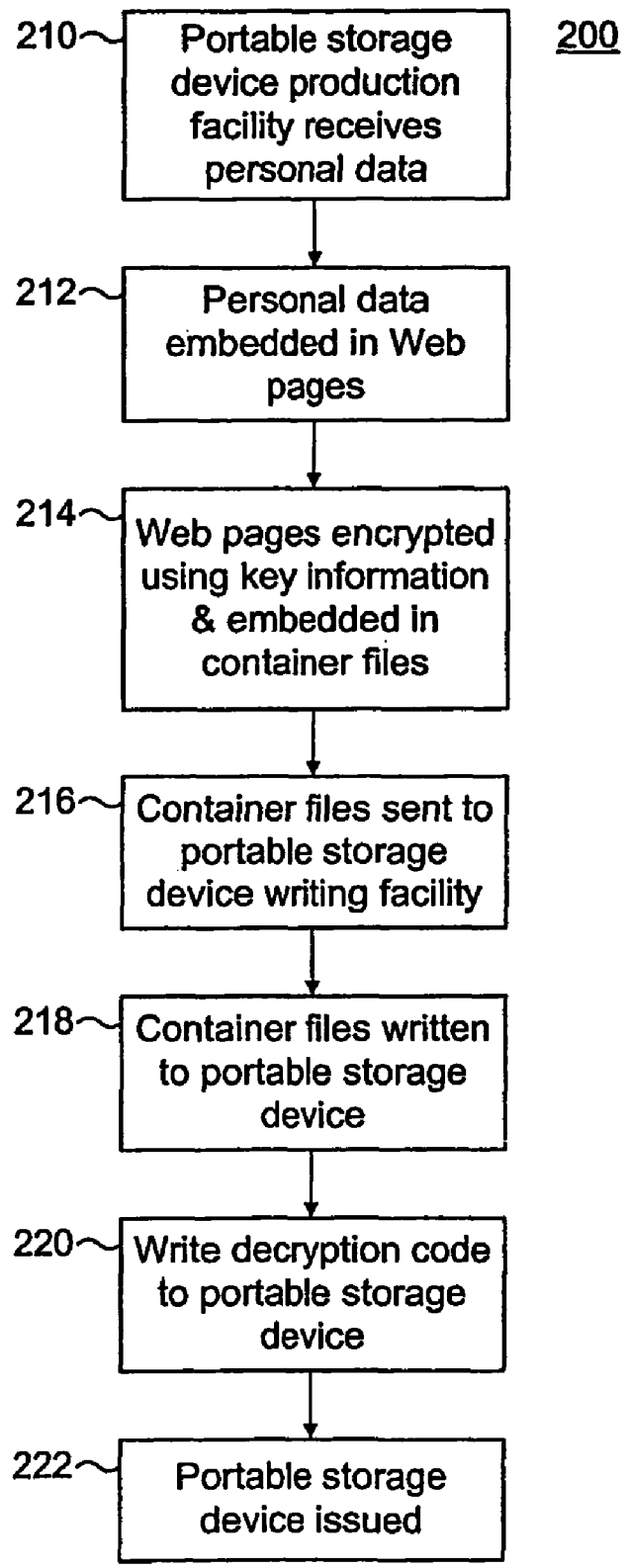
FIG. 3 is a flow diagram showing the steps involved in generating encrypted personal data for storage on a personal storage device, and writing the encrypted data to the personal storage device.

A method 200 for producing a portable storage device for use with preferred embodiments of the invention will now be described with reference to FIG. 3 of the drawings.

The first step 210 of the method 200 involves the portable storage device production facility 16 receiving personal data 26 relating to an individual 28 from the server computer 14 via the secure connection 20. The personal data 26 is then embedded at Step 212 in Web pages 46 at the Web page production facility 32. Also embedded in a separate Web page 46 are access codes to enable a user to address and access personal data 26 held at the remote storage facility via the Internet 24. These access codes determine whether or not there is an Internet connection between the client 12 and the server 14, and can be written in a scripting language such as Javascript code or any other suitable language.

The layout and interaction of the Web pages 46 produced at the Web page production facility 32 depends on the personal data 26 itself, and the manner in which it is to be displayed. For example, a personal data record 48 comprising only a few lines of data could be embedded in a single Web page 46. However, large and unwieldy personal data records 48 should sensibly be divided into smaller sections, each section being embedded in a separate Web page 46. Personal data 26 could thus be presented in a logical fashion by linking multiple Web pages by hyperlinks, enabling a user to navigate the personal data record 48 with ease.

The Web pages 46 are then encrypted at Step 214 using the encryption password 36 that has been provided by the data owner 28, and embedded in unencrypted container HTML files 60. The unencrypted container files 60 are then sent at Step 216 to the portable storage device writing facility 34, and file 60 is written at Step 218 to a portable storage device 42. If, for example, the portable storage device 42 is a CD-ROM, Step 218 will involve "burning" the Web page data onto the CD-ROM.

In addition to the container files 60 which contain encrypted Web pages 38, code which implements the decryption engine 40 is written at Step 220 to the portable storage device. An example of the decryption engine 40 in pseudo-code format is shown in FIG. 4a. This code is written in a scripting language such as Javascript and is identical to the encryption engine code which is used to encrypt personal data 26 at the data storage facility. The decryption engine 40 code exists in plain text on the portable storage device 42, and is therefore freely readable by anyone in possession of the device. However, the decryption routine cannot be implemented without the encryption key 36 used to encrypt the personal data 26.

The portable storage device 42 is now ready to be issued at Step 222 to the owner of the data (or to an authorised third party 45).

In another embodiment of the invention, newly created Web pages 46 can be sent to the database 18 (or to the server 14 if it has data storage facilities) from the Web page production facility 32. The advantage of this feature is that if a data owner 28 wishes to make minor amendments to his personal data 26, the stored Web pages 46 may be sent back to the Web page production facility 32 for the corrections to be carried out without the need for creating entirely new Web pages. These Web pages 46 may be stored on the database 18 in either an encrypted or an unencrypted format.

Figure 5:
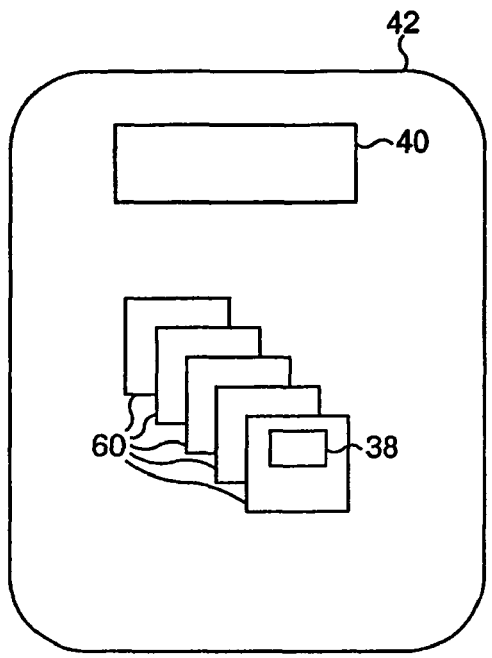
FIG. 5 is a schematic representation showing the data stored on the portable storage device.

A schematic representation of a portable storage device 42 is shown in FIG. 5. The portable storage device 42 shown carries personal data 26 in the form of multiple unencrypted container files 60 which include encrypted Web pages 38 and an encrypted Web page holding access codes for accessing the data storage facility via the Internet 24. The portable storage device 42 also carries a decryption engine 40 for decrypting the encrypted Web page data 38 upon provision of a password 36 which is not stored on the device 42 itself.

The decryption engine 40 also includes codes (not shown) to check the current date against an expiry date set into the portable storage device 42. If the expiry date has been exceeded, the decryption engine 40, upon being run, advises the individual 28 of this fact and does not decrypt the encrypted Web pages 38. This mechanism ensures that personal information stored on the portable storage device 42 cannot be used beyond its usable life. As well as embedded personal data 26, an encrypted Web page 38 may include a hyperlink to initiate a connection between the client computer 12 on which the portable storage device 42 is being "played", and the server computer 14 hosting the data storage facility.

Figure 6:
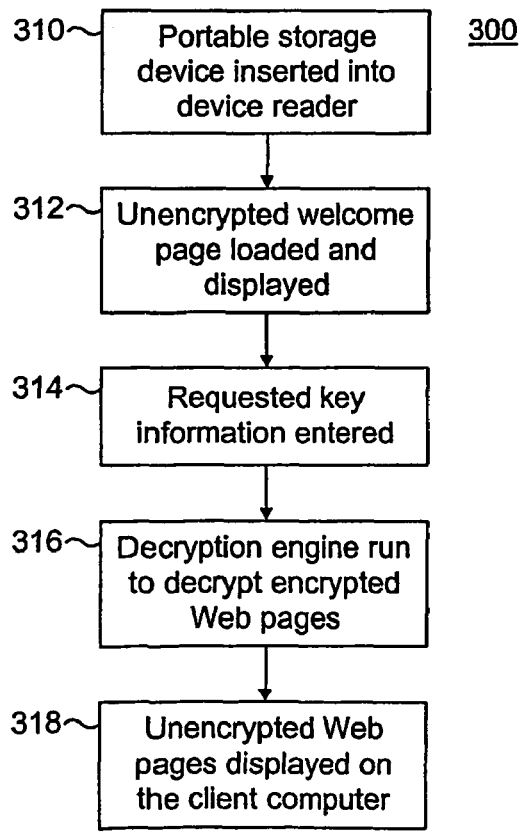
FIG. 6 is a flow diagram showing the steps involved in accessing data from the portable storage device.

The method 300 by which personal data 26 relating to an individual 28 is requested and securely accessed using the portable storage device 42 is now described with reference to FIG. 6 of the drawings.

At step 310 of the method a user (which may be the data owner 28 himself or an authorised third party 45) inserts the portable storage device 42 into a portable storage device reader 13 provided by the client computer 12. An unencrypted start-up Web page is automatically loaded from the portable storage device 42 (using, for example, the standard Microsoft Windows™ auto-run facility) and displayed on the client computer at Step 312 thereby creating an environment within which the portable storage device will run.

The start-up page displays a request for the user's encryption password 36. The user then enters at Step 314 the requested information and hits the return key. If this encryption password 36 is correct, the scripting language (e.g. Javascript) decryption code is executed at Step 316 to unlock the encrypted Web pages 46.

As can be seen from the pseudo-code shown in FIG. 4a, the decryption engine 40 takes as its input the user's encryption password 36, and a decryption algorithm is executed using this password to decrypt the encrypted Web pages 38. In this example, the public domain algorithm "Blowfish" is used. This algorithm is widely regarded as being extremely secure. However, any other suitable encryption/decryption algorithm which provides a suitable level of security may be used. The encryption algorithm creates new unencrypted Web pages 46 "on the fly" which are temporarily stored on the client computer 12. Thus, no personal data 26 remains on the client computer 12 once the portable storage device 42 has been removed from the portable storage device reader 13. The unencrypted Web pages 46 are then displayed at Step 318 on the client computer's Web browser 15 so that the user can view the personal data 26.

As mentioned previously, each encrypted Web page 38 which contains personal data 26 is contained within an unencrypted HTML file 60 (a "container file") which also contains a reference to the decryption scripting language (e.g. Javascript) program 40. When the unencrypted container file 60 is loaded by the Web browser 15, a copy of the decryption algorithm code 40 is loaded into the Web browser at the same time. The container file 60 then runs the decryption algorithm code 40 on the encrypted Web page 38 contained within it. An unencrypted Web page 46 is created on the fly by carrying out the command "document.write(strOutBuf)" which is shown in FIG. 4a. The HTML source code of an example container file 60 is shown in FIG. 4b.

Referring now to FIG. 4b, the reference 'src="bfish.js' of line 3 of the code loads a copy of the decryption algorithm code 40 into the container file 60. Lines 7 and 8 show a series of seeming random alphanumeric characters which represent an encrypted Web page 38 in which personal data 26 has been embedded. Line 13 of the code decrypts the encrypted Web page 38 using the individual's encryption password 36. If the encryption password 36 has not been entered, or is incorrect, the encrypted Web page 38 will not decrypt correctly and will therefore not be displayed in the Web browser 15.

Despite being referred to as a client computer 12, it will be realised that no connection to the Internet 24 is required to securely access personal data 26 stored on the portable storage device 42. The computer 12 may therefore be a non-networked (i.e. standalone) personal computer or other standalone computing device which is capable of reading portable storage devices 42.

Figure 7:
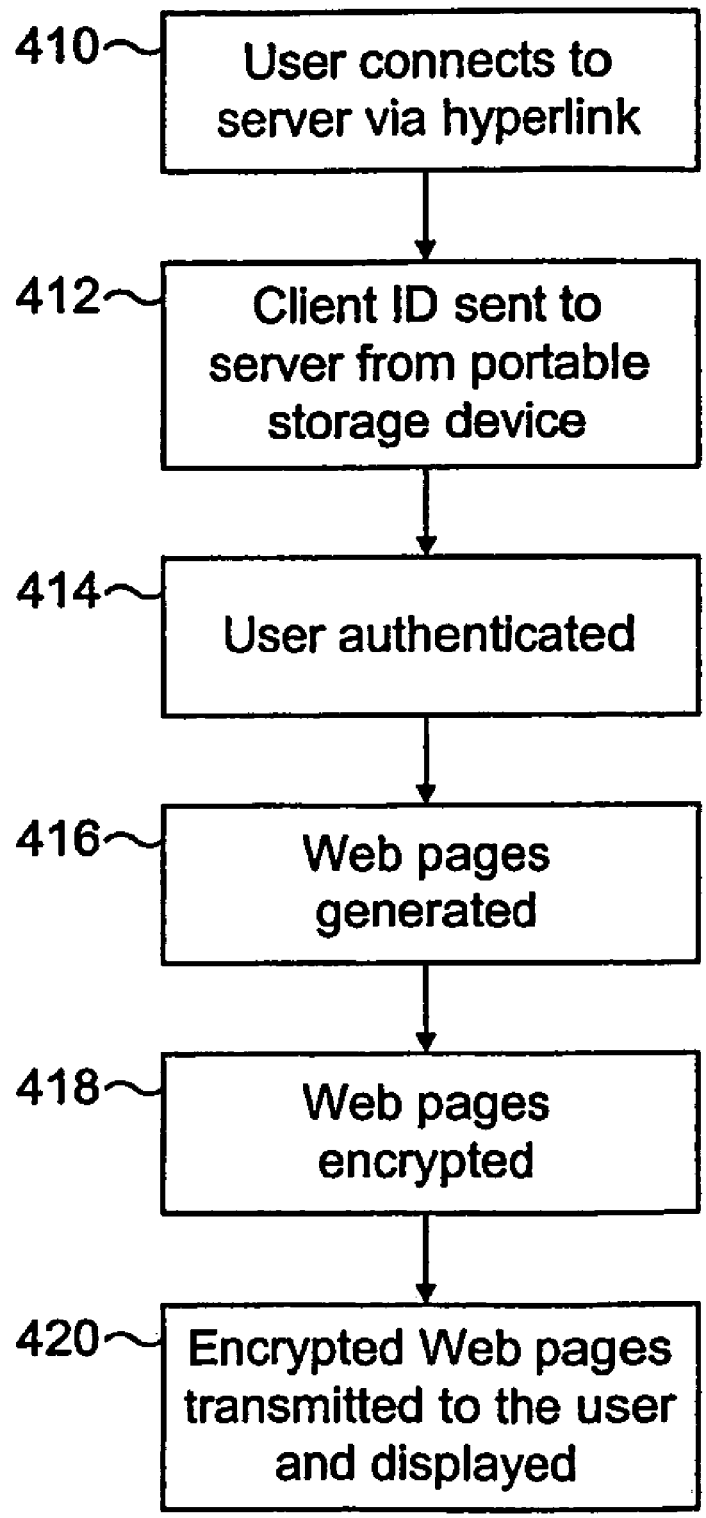
FIG. 7 is a flow diagram showing the steps involved in accessing data from the data storage facility using the portable storage device.

It may be the case that additional, more recent personal data 26b is available at the remote storage facility than is stored on the portable storage device 42. If so, a further method 400 may be provided to access this additional data 26b, as illustrated by FIG. 7. It is assumed here that the user has already inserted the portable storage device 42 into the reader 13, and all the steps of the previously described method 300 have been carried out. It is also taken for granted that during Step 316, the Web page containing codes to access the remote storage service has also been decrypted. In order to access additional data 26b, the user clicks at Step 410 onto a hyperlink to connect to the server computer 14. Next, the user's ID is sent at Step 412 from the portable storage device 42 to the server 14 and hence to the data storage facility.

The user ID is then examined at Step 414 at the Web page production facility 32 to validate the user and therefore the portable storage device's authenticity. If the portable storage device is found to be authentic, new Web pages 46 containing the additional personal data 26b are generated at the Web page production facility 32 (Step 416). The newly generated Web pages 42 are then encrypted at Step 418 by the encryption engine 30 using the encrypted password 36. The encrypted Web pages are subsequently transmitted at Step 420 to the user via a secure Internet connection and displayed in the user's Web browser 15. In this manner, additional data may be displayed at the client computer using the portable storage device 42 as a means to access this data.

Two examples which utilise some of the aforedescribed embodiments of the present invention are now described with reference to FIGS. 7 and 8. The first example relates to the secure access of medical data from the portable storage device 42 in a consultation between a patient 28 and her doctor or physician 45.

Many individuals find that different doctors, regardless of their speciality, require the same information. Providing this same information again and again is time consuming from the point of view of the patient and the doctor. Medical questions are usually asked of patients when the patient does not feel at their best. Unless the patient carries a file containing their medical records to a consultation, they will have to rely on their memory for details of their medical history, and their memory may have deteriorated as the result of their illness or the stress of the consultation itself. The ability to hand over a portable storage device 42 of the type described herein, the contents of which can be printed in the doctor's surgery, will provide significant benefits both to the patient and the doctor.

Personal data relating to an individual 28 which constitutes a personal medical record 48 is illustrated in FIGS. 8a to 8e in plain text format. FIG. 8a sets out the personal details of the individual 28 to whom the data 26 relates, such as their name, address, age, height and weight FIG. 8b shows particulars of the individual's next of kin, general practitioner (medical doctor) details, allergies which the individual has, and details of medication, both past and present. Details of medical events in the individual's life (which include medical investigations undergone by the individual) are illustrated in FIG. 8c.

Medical specialists to whom the individual 28 has been referred are shown in FIG. 8d. In this case, the individual has consulted a specialist for diagnosis and treatment of her diabetes, and an orthopaedic surgeon for treatment of a broken limb. FIG. 8b also lists dates of referrals to these specialists. FIG. 8e shows details of immunisations that the individual has received, together with eye test results, and lifestyle details. Of course, the data record 48 will vary from individual to individual, and will most likely change during an individual's lifetime.

In this example, the individual 28 to whom the medical data 26 relates is a "Ms Mary Elizabeth Brown" aged 44. It can be seen from the portions of the data record illustrated in FIGS. 8b and 8c, that this individual is a diabetic, and that she was diagnosed in 1993 by a diabetic specialist by the name of Dr. Andrew Lane of Harley Street, London. Ms. Brown has been prescribed a thrice daily dose of Metaformin 500 mg to treat her condition (see FIG. 8b). Results of tests carried out in 1993 to diagnose her condition also appear on her medical record 48 (see FIG. 8c). The data displayed in FIG. 8b also shows that this individual reacts severely to nuts, and that she carries an EpiPen® for treating anaphylaxis in case of nut ingestion.

The individual (or patient) visits her general medical practitioner (GP) and takes her personal storage device 42 with her, the device containing a medical record 48 in the form of encrypted Web pages 38 and the decryption engine 40 scripting language (e.g. Javascript) code. In the consulting room, the GP inserts the patient's device 42 into the reader 13 of a conventional personal computer. A Web browser 15 is automatically started up and the unencrypted "start-up" of the patient is displayed (shown in FIG. 9d).

Figure 9A:
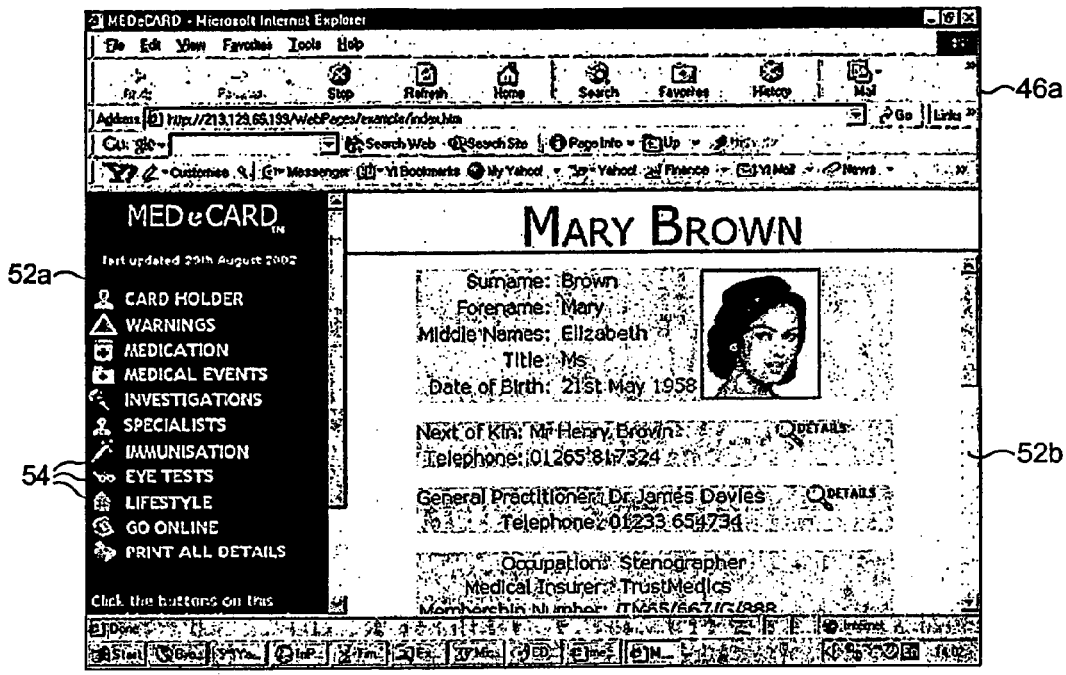
FIGS. 9a to 9c are screen-shots of Web pages showing parts of the personal data record of the patient shown in FIG. 8.
Figure 9B:
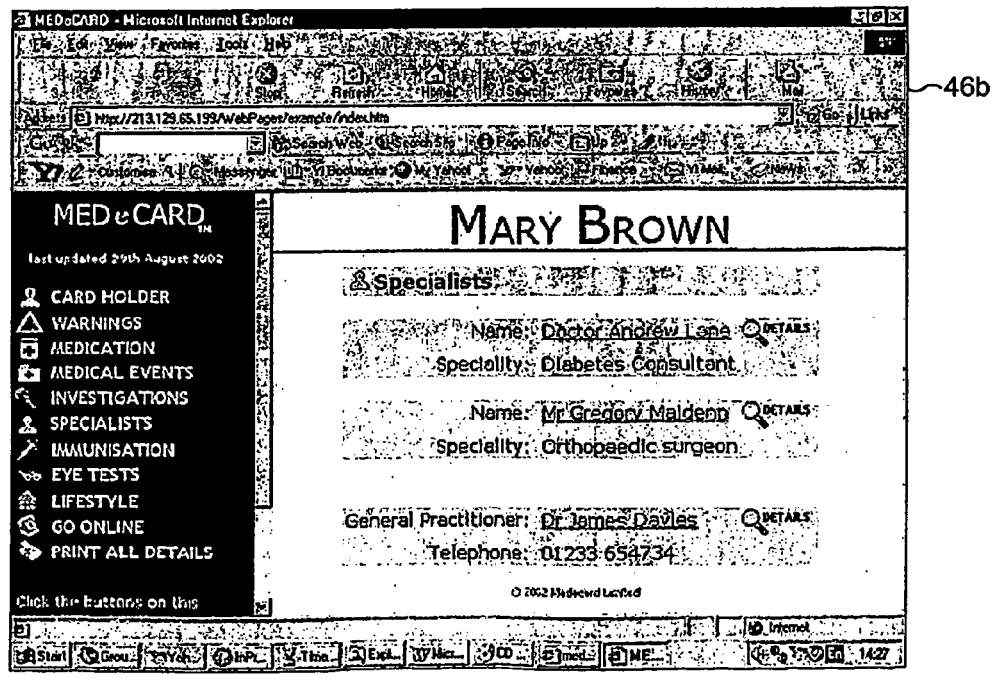

The patient tells the doctor her password 36 which the doctor duly enters into the appropriate part of the start-up Web page. The doctor clicks on the "OK" button displayed on the start-up page initiating the decryption of the encrypted data. As described above, this is carried out by running the 40 scripting language (e.g. Javascript) decryption code 40 on the Web browser 15, using the encryption password 36 as a decryption key. When the decryption process is complete, the first page 46a of the patient's unencrypted medical record 48 is displayed in the user's Web browser 15, as shown in FIG. 9a. Web page 46a includes a first frame 52a which displays a menu for navigating the displayed medical record 48, and a second frame 52b for displaying the medical data 26 itself. Menu buttons 54 may be clicked on by the doctor to display the required data. For example, clicking on the "Specialists" button displays the Web page 46b shown in FIG. 9b, in which the names and specialities of the doctors which have been consulted by the patient, and her GP detail, are displayed.

The consultation takes place and the patient presents with symptoms which are associated with complications due to diabetes. The doctor notes from the medical records displayed in her Web browser 15 that the patient 28 has diabetes and that she is currently taking medication for her condition. The patient informs her doctor that she has had some investigative tests undertaken in hospital recently, the results of which have not yet been stored on the device 42. The doctor clicks on the "go online" button displayed in the menu shown in FIGS. 9a and 9b, enters the correct user ID, and is connected to the server computer 14 and hence the data storage facility. Encrypted additional test data 26b requested by the doctor 45 is sent from the data storage facility to the doctor's computer via the Internet 24. This encrypted data is then decrypted by the decryption engine 40, and is finally displayed in the doctor's Web browser. The test results indicate that the dosage of the patient's medication should be increased, and the doctor writes out a new prescription accordingly. As the doctor is currently online and connected to the data storage facility, she could go to an "amend data" Web page (if such a page is provided) and amend the medication details.

In the second example, the use of an embodiment of the invention which relies on a generic password in an emergency situation is described. A generic password (i.e. one that is not private to the data owner 28 but which has been issued to an authorised third party 45) is used to encrypt medical data 26 relating to the individual 28. The generic password may be generated by the data storage facility and issued to medical personnel directly. Alternatively, a health authority, department, or hospital etc may choose the password which is forwarded to the data storage facility to be used as the generic password.

As the generic password could enable a large group of people to view the individual's medical data, it is essential that only the most important parts of the individual's personal data record (i.e. those for which freedom of access outweighs the presumption of confidentiality) are encrypted using this generic password. As described previously, this functionality is provided by a security level indicator that is associated with each piece of personal data relating to an individual stored at the data storage facility.

The patient can also choose to include unencrypted pages on her personal storage device 42 and/or the generic password may be provided on the portable storage device to enable all third parties to access data encrypted using the generic password, whether or not authorisation has been given.

Now consider the situation where Ms. Brown collapses and, on being examined, is found to be unconscious. An ambulance is called to the scene, and it is found that Ms. Brown is carrying a portable storage device 42 carrying encrypted medical data 26 in accordance with the present invention. To read the medical data stored on the device 42, the ambulance crew insert the device into a device reader 13 of, for example, a laptop. The patient's start-up Web page is displayed in the laptop's Web browser 15, and the generic password issued in advance is entered. The generic password is used by the decryption engine 40 stored on the device 42 to decrypt the relevant parts of Ms. Brown's medical record which have been encrypted using this generic password, and the relevant decrypted personal data is displayed.

Figure 9C:
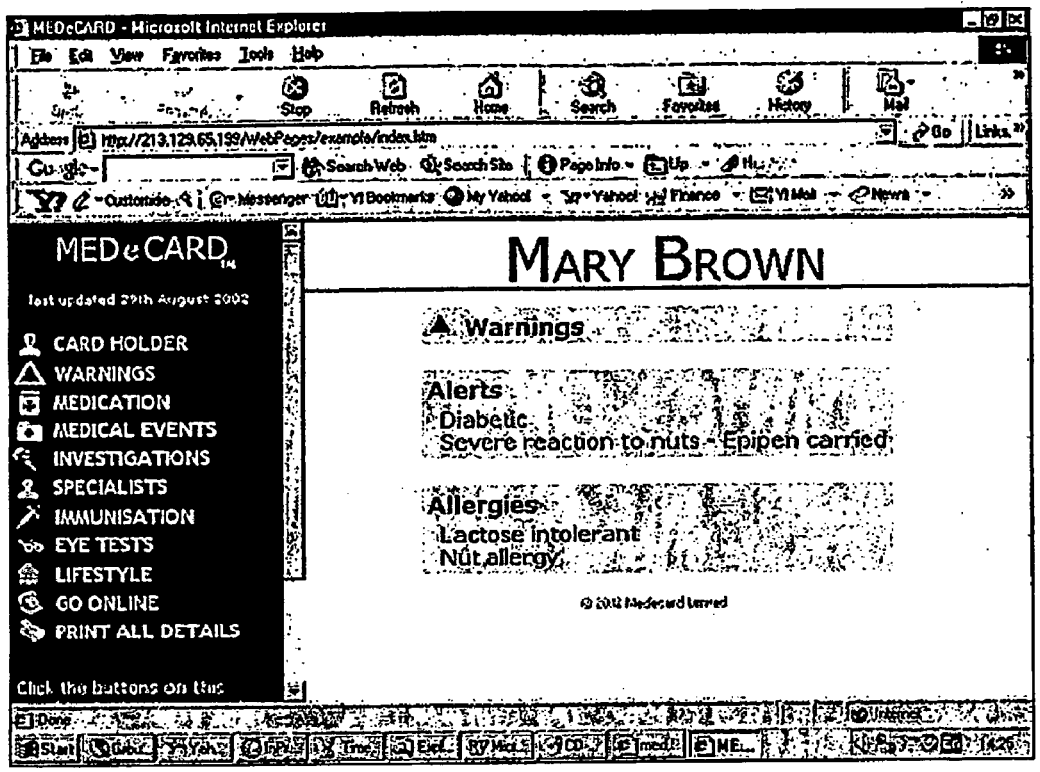
Figure 9D:
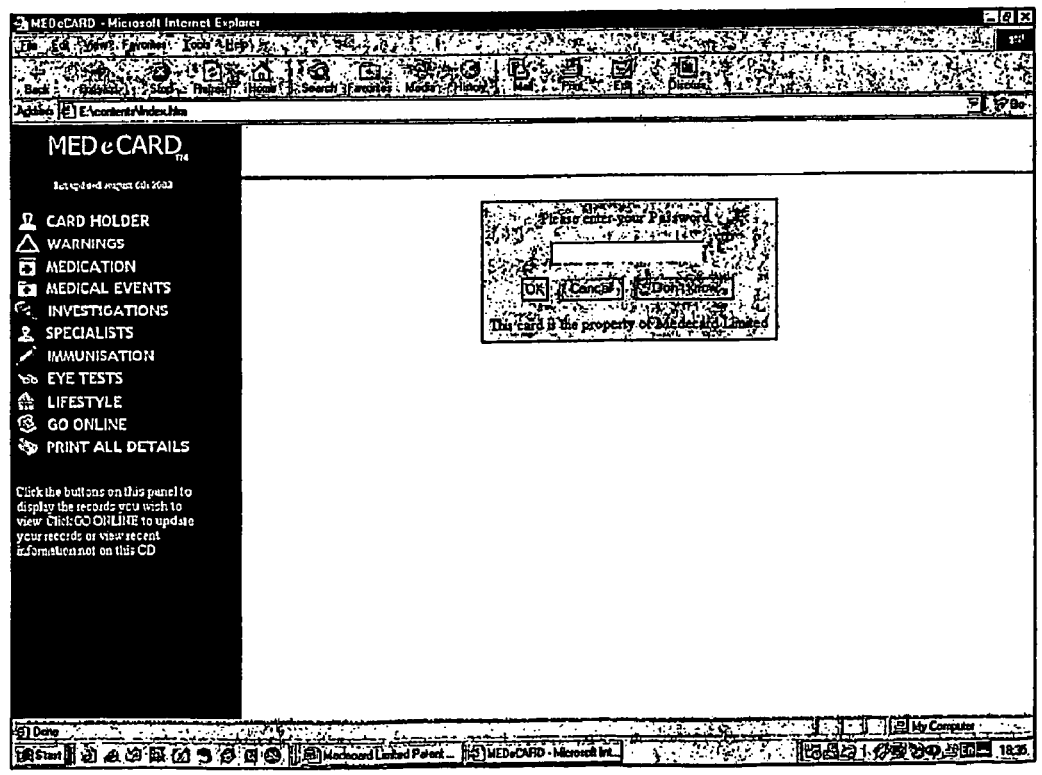
FIG. 9d is a screen-shot of a Web page displayed to a user for entering a decryption password to access data stored on the portable storage device.

An example of the medical data displayed is shown in FIG. 9c. The ambulance crew can see from the displayed personal data shown in FIG. 9c that Ms. Brown reacts severely to nuts, and that she is a diabetic. She may thus be suffering from anaphylaxis, or be in a diabetic coma Armed with this information, appropriate tests may be carried out promptly at the scene by the ambulance crew, and the correct treatment given in a timely manner.

When Ms. Brown reaches hospital, her device 42 is inserted into a device reader 13 of, for example, a personal computer located in the Accident & Emergency department. Again, no special software or training of staff is required in order to use this device 42. Medical personnel in the department are able to view parts of the patient's medical record 48 which have been encrypted using the generic password. After the patient has been treated, relevant medical information about the incident may then easily be sent to the data storage facility, this information either being uploaded directly from a personal computer, or test results may be sent to the data storage facility whereupon it may be obtained at a later data using the methods described herein.

Having described preferred embodiments of the present invention, it is to be appreciated that the embodiments in question are exemplary only and that variations and modifications such as will occur to those possessed of the appropriate knowledge and skills may be made without departing from the spirit and scope of the invention as set forth in the appended claims.

The present invention is not restricted to the secure storage of medical data, but may also be used for storing other types of personal data such as personnel data, financial data or company data, in which case the term individual would include a private company or an organisation. For example, companies might use embodiments of the present invention to make personnel records available to their staff. This would meet current employment law and provide a secure method for employees to access their information. Financial advisors could use the invention to for securely storing and accessing a client's financial status (i.e., a wealth check) which can be regularly updated. Also, companies could distribute information relevant to their clients, along with confidential information and set an expiry date on the portable storage device to limit validity of the information. Another application of the present invention could be the storing and accessing of personalised information combined with an organisation's information, e.g., a members card for the duration of the membership period.

Distribution of company confidential information to staff and groups of staff could also be carried out by using the portable storing device acting as a means of access, wherein the availability of the information is constrained by a time limit. A company could even provide the portable storage device to its suppliers as a means of access mechanism for the supplier to be able to communicate and have access to an area of its supplier's database. The portable storage device could contain sensitive information relating to the company and supplier relationship. The supplier could then provide information to the company, the company being able to control, manage and respond to (e.g. order) information provided by its suppliers.

Although the system for implementing the preferred embodiments of the invention has been described in terms of client-server architecture, the client and server communicating via the Internet, it is possible that the components of the system may be part of a local area network, or a private wide area network such as an intranet.

On a reading of the detailed description, it will be apparent to one skilled in this field of technology that the arrangement of components on the server-side of the system 10b can be varied according to user requirements such as the amount of personal data 26 to be stored. For example, one or more additional databases in connection with the server computer 14 may be provided for storing personal data 26. This arrangement would free up client computer resources to handle incoming requests for data storage and access. That is, the server computer could be used solely to manage the handling of data within the data storage facility, rather than storing the data itself.

These additional databases could provide tape facilities capable of storing very large files and hence large amounts of data. By using this type of modular system architecture, the server-side 10b of the system may easily be upgraded to cope with an increased number of users. This would present little or no restriction on the volume of personal data 26 that an individual 28 could hold at the data storage facility, although it would be possible to enforce a physical limit on the amount of storage allowed for a particular individual. It is foreseeable that this function could easily be implemented by charging the individual 28 according to the volume of storage space that he requires.

The method of the invention may also provide for information to be translated into different languages using standard translation packages. An individual could therefore be anywhere in the world and a doctor could view their medical data in their native language. The method may also allow for direct connections to be made from a computing device to an outside service other than the data storage facility.

The invention claimed is:

1. A method of securely storing and accessing personal data relating to an individual, said personal data constituting a personal data record, the method comprising:
coupling a portable data storage device to a computing device for data transfer between them, the storage device carrying an encrypted personal data record and decryption logic for decrypting the encrypted personal data record upon provision of a key not stored on the portable data storage device;
accessing the encrypted personal data record on the storage device and running the decryption logic on the computing device to decrypt the encrypted personal data record upon input of the key to the computing device; and
displaying the decrypted personal data by means of the computing device, wherein the encrypted personal data includes at least one address of a remote data storage facility accessible via the computing device, which, when decrypted by the decryption logic, enables the computing device to address encrypted additional personal data held at the addressed remote data storage facility.

2. The method of claim 1, wherein the decrypted personal data is displayed in read-only form.

3. The method of claim 1, wherein the encrypted personal data further includes at least one access code which, when decrypted by the decryption logic, enables access to the encrypted additional personal data held by the addressed remote data storage facility.

4. The method of claim 1, comprising running the decryption logic on the computing device using the key input to the computing device to decrypt the encrypted additional personal data, and displaying the decrypted additional personal data on the computing device.

5. The method of claim 1, further comprising writing encrypted additional personal data from the remote data storage facility to the portable data storage device via the computing device.

6. The method of claim 1, preceded by uploading personal data to the remote data storage facility and encrypting that data to become the encrypted additional personal data.

7. The method of claim 6, comprising updating the encrypted personal data stored on the portable data storage device by issuing a replacement portable data storage device to a user bearing encrypted personal data that includes encrypted additional personal data.

8. The method of claim 7, comprising checking a date or identity code held by a portable data storage device and preventing access to the personal data stored on the portable data storage device if the date or identity code indicates that access should no longer be allowed because that portable data storage device is out of date or has been superseded.

9. The method of claim 1, comprising uploading encrypted personal data to the remote data storage facility via the computing device.

10. The method of claim 1, comprising issuing a further portable data storage device to a third party bearing an encrypted address of the remote data storage facility which, when decrypted, enables access via the computing device to data held at the addressed remote data storage facility.

11. The method of claim 10, comprising separately issuing a key to the third party enabling decryption of the address.

12. The method of claim 10, comprising recording and auditing third-party access to the addressed remote data storage facility.

13. The method of claim 10, wherein the further portable data storage device also bears an encrypted access code which, when decrypted, enables access to the data held at the addressed remote data storage facility.

14. The method of claim 13, wherein the access code enables access to a specific level of data deemed appropriate to the third party that receives the further portable storage device, by correlation with a security level indicator attached to each record within the remote data storage facility.

15. The method of claim 13, comprising separately issuing a key to the third party enabling decryption of the access code.

16. The method of claim 1, wherein the portable data storage device also carries unencrypted personal data for display without decryption when the portable data storage device has been coupled to the computing device.

17. The method of claim 1, wherein the storage device is not capable of running the decryption logic and displaying the personal data.

18. The method of claim 1, wherein the portable data storage device carries logic for launching a program on the computing device to display unencrypted or decrypted personal data when the portable data storage device has been coupled to the computing device.

19. The method of claim 1, wherein the portable data storage device carries the encrypted personal data embedded in a page viewable, when unencrypted or decrypted, by an Internet browser running on the computing device.

20. A system for securely storing and accessing personal data relating to an individual, said personal data constituting a personal data record, the system comprising:
a portable data storage device carrying an encrypted personal data record and decryption logic for decrypting the encrypted personal data upon provision of a key not stored on the portable data storage device;
a computing device to which the portable data storage device can be coupled for data transfer between them, the computing device including logic for accessing the encrypted personal data record on the storage device, and logic for running the decryption logic to decrypt the encrypted personal data record upon input of the key to the computing device; and
a display associated with the computing device for displaying the decrypted personal data, wherein the portable data storage device includes logic for addressing and accessing a remote storage facility via the computing device to enable the computing device to address encrypted additional personal data held at the addressed remote data storage facility.

21. The system of claim 20, wherein the computing device includes logic for running the decryption logic using the key input to the computing device to decrypt the encrypted additional personal data, and logic for displaying the decrypted additional personal data.

22. The system of claim 20, wherein the remote data storage facility includes logic for writing encrypted additional personal data to the portable data storage device via the computing device.

23. The system of claim 20, further comprising logic for uploading personal data to the remote data storage facility and logic for encrypting that data to become the encrypted additional personal data.

24. The system of claim 23, further comprising logic for updating the encrypted personal data stored on the portable data storage device by issuing a replacement portable data storage device to a user bearing encrypted personal data that includes encrypted additional personal data.

25. The system of claim 24, comprising logic for checking a date or identity code held by a portable data storage device and logic for preventing access to the personal data stored on the portable data storage device if the date or identity code indicates that access should no longer be allowed because that portable data storage device is out of date or has been superseded.

26. The system of claim 20, comprising logic for uploading encrypted personal data to the remote data storage facility via the computing device.

27. The system of claim 20, comprising a further portable data storage device issued to a third party bearing an encrypted address of the remote data storage facility which, when decrypted, enables access via the computing device to data held at the addressed remote data storage facility.

28. The system of claim 27, wherein the further portable data storage device also bears an encrypted access code which, when decrypted, enables access to the data held at the addressed remote data storage facility.

29. The system of claim 28, comprising a key separately issued to the third party enabling decryption of the access code.

30. The system of claim 27, comprising data access logic for enabling access to a specific level of data deemed appropriate to the third party that receives the further portable storage device, by correlation with a security level indicator attached to each record within the remote data storage facility.

31. The system of claim 27, comprising a key separately issued to the third party enabling decryption of the address.

32. The system of claim 27, comprising logic for recording and auditing third-party access to the addressed remote data storage facility.

33. The system of claim 20, wherein the portable data storage device also carries unencrypted personal data for display without decryption when the portable data storage device has been coupled to the computing device.

34. The system of claim 20, wherein the storage device is not capable of running the decryption logic and displaying the personal data.

35. The system of claim 20, wherein the portable data storage device carries logic for launching a program on the computing device to display unencrypted or decrypted personal data when the portable data storage device has been coupled to the computing device.

36. The system of claim 20, wherein the portable data storage device carries personal data embedded in a page viewable, when unencrypted or decrypted, by an Internet browser running on the computing device.

37. A portable data storage device carrying encrypted personal data and decryption logic for decrypting the encrypted personal data upon provision of a key not stored on the portable data storage device, and being co-operable with a computing device to which the portable data storage device can be coupled for data transfer between them, whereby the computing device can access the encrypted personal data on the portable data storage device, run the decryption logic to decrypt the encrypted personal data upon input of the key, and drive an associated display to display the decrypted personal data, wherein the portable data storage device further includes logic for addressing and accessing a remote storage facility via the computing device to enable the computing device to address encrypted additional personal data held at the addressed remote data storage facility.

38. The device of claim 37, wherein the encrypted personal data is embedded in a page viewable, when unencrypted or decrypted, by an Internet browser running on the computing device.

39. The device of claim 38, wherein the decryption logic includes scripting language code for decrypting encrypted pages.

40. The device of claim 37 and further including a date or identity code for checking to prevent access to the personal data if the code indicates that access should no longer be allowed because that device is out of date or has been superseded.

41. The device of claim 37 and also carrying unencrypted personal data for display without decryption when the portable data storage device has been coupled to the computing device.

42. The device of claim 37 and not being capable of running the decryption logic and displaying the personal data.

43. The device of claim 37 and also carrying logic for launching a program on the computing device to display unencrypted or decrypted personal data when the device has been coupled to the computing device.

* * * * *